United States Patent [19]

Lannertone

[11] Patent Number: 4,903,689

[45] Date of Patent: Feb. 27, 1990

[54] SHOULDER SUPPORT SYSTEM WITH BREAST STRESS RELIEVER FOR A CHIROPRACTIC OR MEDICAL TREATMENT OR MASSAGE TABLE

[76] Inventor: Marc W. Lannertone, 433 E. Napa St., Sonoma, Calif. 95476

[21] Appl. No.: 299,756

[22] Filed: Jan. 23, 1989

Related U.S. Application Data

[63] Continuation-in-part of Ser. No. 154,915, Feb. 11, 1988, abandoned.

[51] Int. Cl.$^4$ .................................... A61F 5/00

[52] U.S. Cl. .................................... 128/72; 128/70

[58] Field of Search .................................... 128/70-74, 128/69, 75; 269/322-327, 328; 272/144, 134; 378/37, 209, 208; 5/66, 431, 462

[56] References Cited

U.S. PATENT DOCUMENTS

| | | | |
|---|---|---|---|
| 1,282,580 | 10/1918 | Stedman | 128/71 |
| 1,427,004 | 8/1922 | McManis | 128/73 |
| 1,499,013 | 6/1924 | Gunther | 128/72 |
| 1,577,785 | 3/1926 | Castetter | 128/72 |
| 2,693,796 | 11/1954 | Warner | 128/70 |
| 3,643,938 | 2/1972 | Levasseur | 269/328 |
| 3,795,018 | 3/1974 | B//aded | 5/68 |
| 4,054,960 | 10/1977 | Pettit et al. | 5/357 |
| 4,508,109 | 4/1985 | Saunders | 128/75 |

FOREIGN PATENT DOCUMENTS

| | | | |
|---|---|---|---|
| 3236228 | 4/1984 | Fed. Rep. of Germany | 378/208 |
| 1119944 | 6/1956 | France | 269/328 |
| 1227194 | 4/1986 | U.S.S.R. | 269/328 |

*Primary Examiner*—Edgar S. Burr
*Assistant Examiner*—Huong Q. Pham
*Attorney, Agent, or Firm*—Owen, Wickersham & Erickson

[57] ABSTRACT

A shoulder support system for a chiropractic or medical treatment or massage table. This table may have a main upper surface with a well or wells extending down throughout or it may have a plurality of table members. It includes two shoulder support members with a recess between them. A patient lying properly face down on the table is supported by the shoulders in contact with the shoulder support members. Where the patient is a woman, her breasts rest in the recess between the shoulder support members, being supported out of contact with the table, so that the table does not exert substantial force on her breasts. The shoulder supports are mounted on a base which may be supported by the table substructure at adjustable heights. The shoulder support members may be adjustable laterally, so that the distance between them can be varied to accommodate patients with different shoulder widths and breast sizes, all relative to the plane on which the patient is lying. Each shoulder support member may be mounted on a bracket which is slidably mounted for movement laterally with respect to the table.

13 Claims, 5 Drawing Sheets

FIG._1
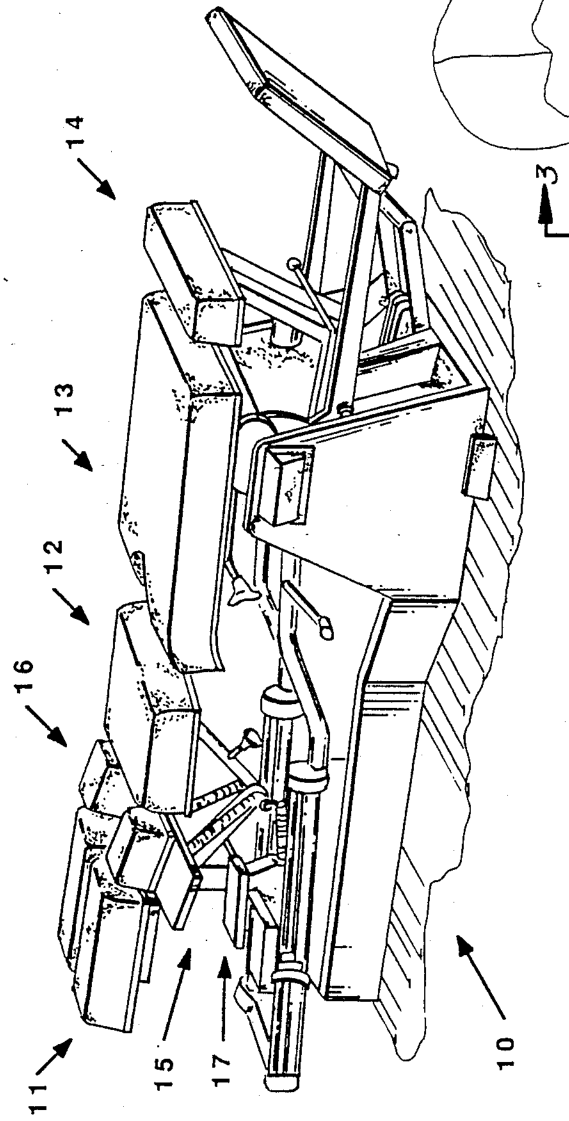
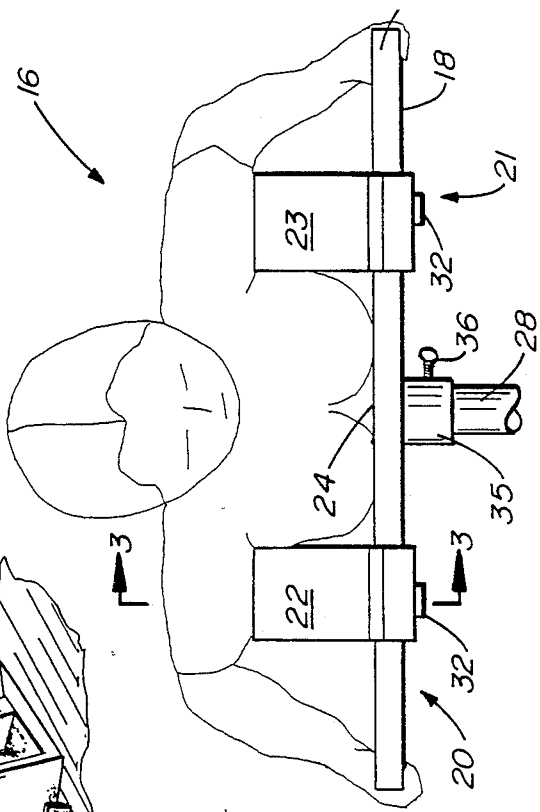
FIG._2

SHOULDER SUPPORT SYSTEM WITH BREAST STRESS RELIEVER FOR A CHIROPRACTIC OR MEDICAL TREATMENT OR MASSAGE TABLE

CROSS REFERENCE TO A RELATED APPLICATION

This application is a continuation-in-part of application Ser. No. 154,915 filed Feb. 11, 1988.

The present invention relates to chiropractic and medical treatment tables, and to massage tables and, more particularly, to a shoulder support attachment system with breast stress reliever, for a chiropractic or medical treatment or massage table on which a patient lies, often face down.

BACKGROUND OF THE INVENTION

Chiropractic, and much medical, treatment and massage are commonly performed with the patient lying on a specially designed treatment table, which has a number of independently adjustable support surfaces. The support surfaces can each be adjusted in position to provide proper support for the particular patient and the particular treatment.

During the course of treatment, the chiropractor, masseur, or doctor may exert substantial force on the patient, forcing the patient against the treatment table. Although the table support surfaces are fully padded, the resultant force exerted by the table on the patient may cause discomfort to some sensitive body areas. When the patient is a woman and when the treatment demands that she lie face-down and on her stomach, the resulting force tends to press the patient's breasts against the table and may cause substantial discomfort. This problem of discomfort during treatment is particularly troublesome for heavily busted women, women with breast implants, women who have undergone mastectomies, or male patients who have any one of a number of types of chest surgeries.

A number of chiropractic treatment tables provide vertically and longitudinally adjustable support surfaces for a chiropractor to administer treatment. Some tables used during medical treatment also include adjustable parts.

An object of the present invention is to provide special support apparatus, for chiropractic or medical or massage treatment, which enable women patients to lie face-down during treatment, even pressed down by the chiropractor, without incurring painful pressure to their breasts, by providing stress relief for the breasts.

Another object of the invention is to provide support for a chiropractic or medical treatment or massage table, whereby the shoulders can help support a woman patient lying on her stomach on the table, with her head, legs, midsection and other portions lying on the table, the shoulder supports providing a recess accommodating the patient's breasts to provide breast stress relief by retaining them above a base area of the table. Similar relief may be provided for pregnant women.

Another object is to provide proper support and resistance adjustment of the thoracic spine for prone women patients.

Another object of the invention is to provide an improved chiropractic, medical treatment, or massage table which supports a woman patient lying face down without producing pressure on her breasts.

Other objects, advantages and features of the invention will become apparent from the following description of preferred embodiments, considered along with the accompanying drawings.

SUMMARY OF THE INVENTION

A treatment table of the present invention is provided with a pair of laterally adjustable shoulder supports, which treatment from the chest area. The shoulder supports provide the necessary support for treatment and provide a recess to receive the upper chest area, because the shoulder supports are spaced apart at a readily adjustable distance, so that substantially no force is exerted by the table on the chest area. The shoulder support system is particularly useful to increase the comfort of a woman patient having treatment administered while lying prone or face-down or on her stomach. Her body is supported flat along substantially a plane. The recess between the shoulder supports provides a place in which the patient's breasts can be held above the table's base surface there and out of contact with it. Substantially no force is exerted thereon, either by the treatment table or by the chiropractor or doctor. In addition to providing stress relief for breasts, similar assistance may be provided to pregnant women.

The shoulder support system supplements the supply for the rest of her body, especially when patient lies face-down, includes two shoulder support members, providing a recess between them and a base on which the shoulder support members are mounted for lateral movement. In use, the shoulder support members are adjusted so that they properly support the particular patient. When a patient lies face down on the table, the patient's shoulders are supported on the shoulder supports, and the chest or the breasts lie in the recess between the shoulder supports. Therefore, no force is exerted by the table or the chiropractor or doctor or masseur on the patient's chest or breasts. The added force of treatment is borne by the patient's shoulders and other body parts but not her breasts or his sensitive chest area.

In one embodiment, each shoulder support member is mounted on a bracket which is slidable along a base that forms a bracket track. The shoulder supports and brackets can be moved along the base laterally with respect to the table to provide the proper opening by such adjustment. Enough such width of the recess is important.

The weight transmitted through the shoulders may be sufficient to hold the shoulder supports in place, but, if desired or needed, each bracket may include locking means by which it can be fixed in place along the support track, preventing the shoulder support members from moving during treatment.

Also, if desired, a removable panel may provide similar assistance for a pregnant woman.

The base is held in place by table substructure on the conventional chiropractic or medical treatment table. The support substructure may enable the base of the shoulder support members to be adjusted to various elevations and attitudes with respect to the other table members. Less complex structures may be provided, if desired.

BRIEF DESCRIPTION OF THE DRAWINGS

FIG. 1 is a view in perspective of a chiropractic treatment table having a shoulder support and breast stress-relief system, embodying the principles of the invention, as well as nearly planar support for the rest of the body.

FIG. 2 is a view in front elevation of the shoulder support and breast stress-relief system of FIG. 1, with a similar patient's outline shown in place. The support for the head, legs and other portions is not shown.

DESCRIPTION OF THE PREFERRED EMBODIMENTS

Figure 3:
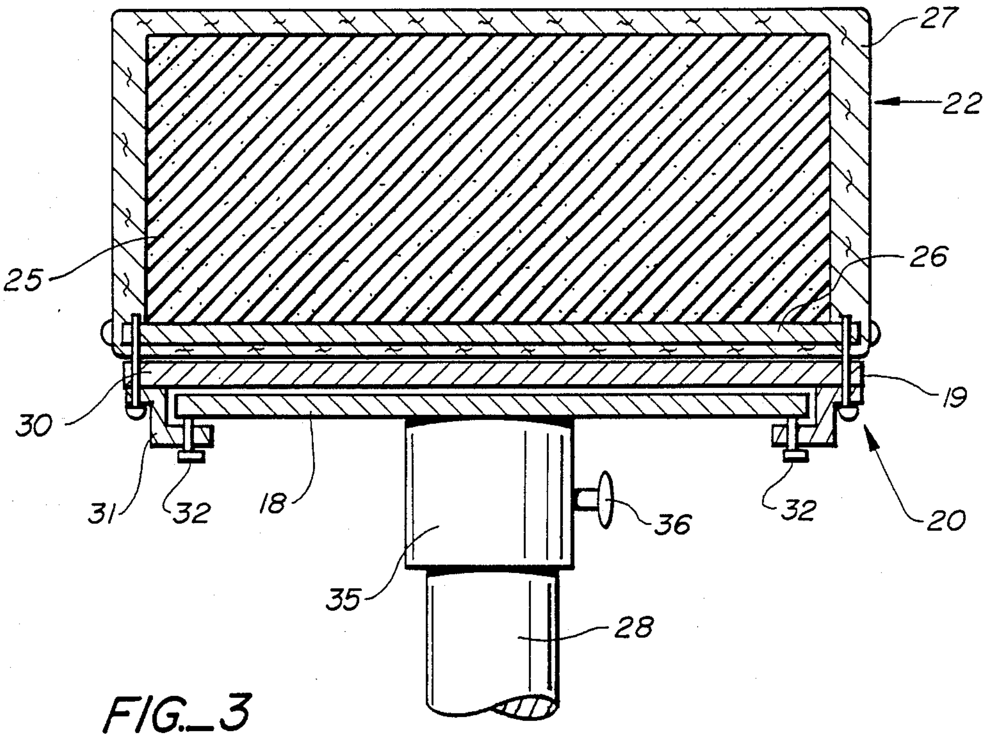
FIG. 3 is an enlarged view in section of one of the support members taken along line 3—3 in FIG. 2.
Figure 7:
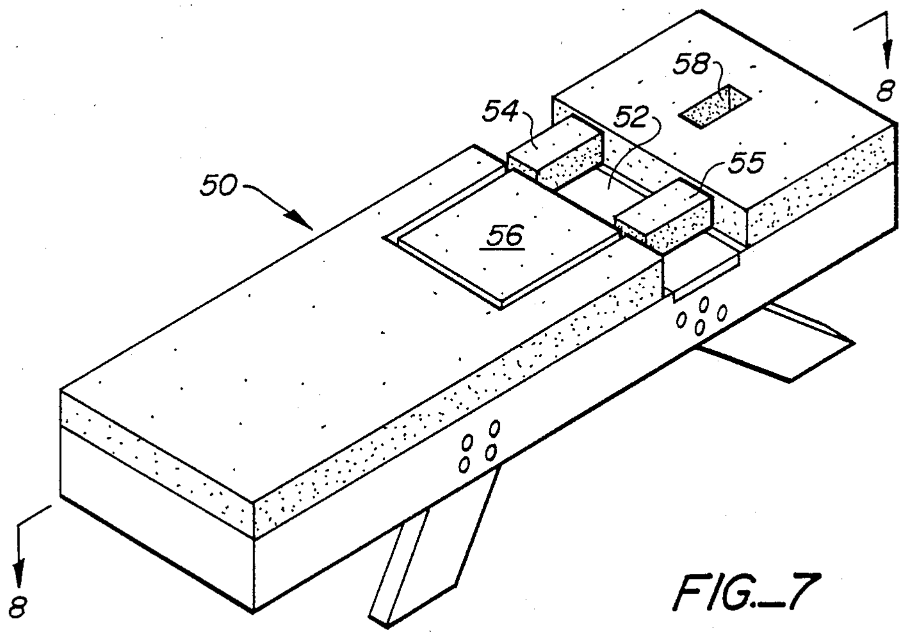
FIG. 7 is a view in perspective of a simpler padded substantially planar table providing shoulder supported breast stress relief.

FIG. 1 shows a chiropractic treatment table 10 that includes a head support 11 on which the head rests, a midsection support 12 on which the midsection rests, a leg support 13 on which the legs rest, and a lower leg support 14. Each of these supports is mounted on a substructure 15, and these supports 11, 12, 13, and 14 can be varied in position to different elevations and slopes with respect to the other support members.

The table 10 also includes a shoulder support system 16 located between the head support 11 and the midsection support 12. The head support 11 may also include at each side a hand rest 17, where the patient's hands may rest. The shoulder support system 16 is mounted on the adjustable support substructure 15, similarly to the mounting of the other support members. As FIG. 2 shows, the shoulder support system 16 includes a base 18 that may be a standard element of the table 10, the base 18 providing at its outer edges a pair of bracket tracks 19, supporting brackets 20 and 21, and shoulder supports 22 and 23.

When a woman lies on her stomach on the treatment table 10 for chiropractic or medical treatment or massage, as shown in FIG. 2, her upper body is supported at her shoulders by the shoulder support members 22 and 23 of the shoulder support system 16. On substantially the same flat plane as the shoulders, the head, midsection and legs are supported. The wide separation between the shoulder support members 22 and 23 creates a sufficiently large recess 24, where the patient's breasts may rest comfortably, without any of her body weight or any force of treatment bearing on the table 10.

As shown in FIG. 3, the shoulder supports 22 and 23 of the invention may include a cushion filler material 25 (like that for the support of other portions of the patient's body) mounted on a rigid base 26 and encircled by upholstering 27. The shoulder supports 22 and 23 extend longitudinally along the table 10 a sufficient distance to provide support along the shoulder and to make the recess 24 of sufficient size to accommodate a woman's breasts. The shoulder supports 22 and 23 also extend above the bracket track 18 a sufficient distance to provide a basic recess depth. For example the shoulder supports 22 and 23, according to one embodiment, may be each about four inches wide, nine inches long, and extend five inches above the base bracket 18.

To provide proper height for the chiropractor's convenience, the base 18 preferably includes an elevator member or shaft 28 mounted at its lower end on the support substructure 15 and mounted at its upper end on the base 18. This structure 28 enables adjustment of the height of the base 18 and, therefore, of the shoulder supports 20 and 21. The shaft 28 may fit into collar 35 and be fastened there by a set screw 36.

The shoulder supports 22 and 23 are each mounted on a bracket 20 or 21, as by screws. Each bracket 20 or 21 is movable along the tracks 19 of the base 18. The brackets 20 or 21 each include a plate 30, which is approximately the same length and width as the shoulder supports 22 and 23, and flange members 31 at either end holds the bracket 20 or 21 in place along the base 18. The brackets 20 and 21 ordinarily are retained in any position to which they are moved by the weight of the pertinent body portions of the patient transmitted through the shoulders. However, if desired, the brackets 20 and 21 may include locking means 32, by which they may be fixed in place at a particular position on the bracket track 19.

The base 18 in one embodiment is comprised of a rigid plate 24 extending transversely of the treatment table 10. The base 18 and the tracks 19 extend far enough to provide a wide range of shoulder support positions to accommodate patients of various sizes comfortably.

Figure 4:
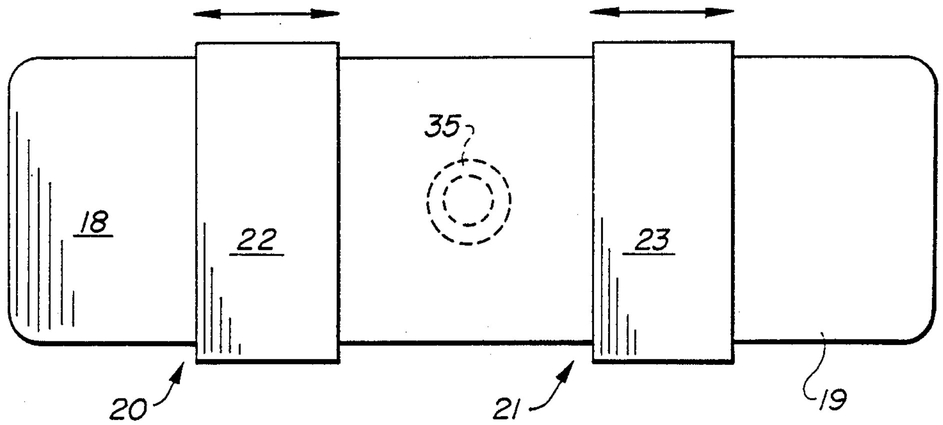
FIG. 4 is a top plan view of the shoulder support system of FIGS. 1-3.
Figure 5:
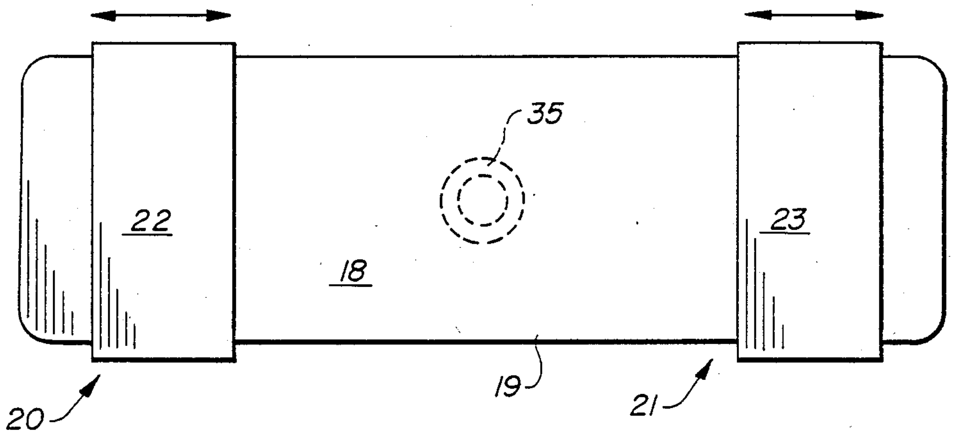
FIG. 5 is a top plan view similar to FIG. 4 but with each of the shoulder supports adjusted to a different position.
Figure 6:
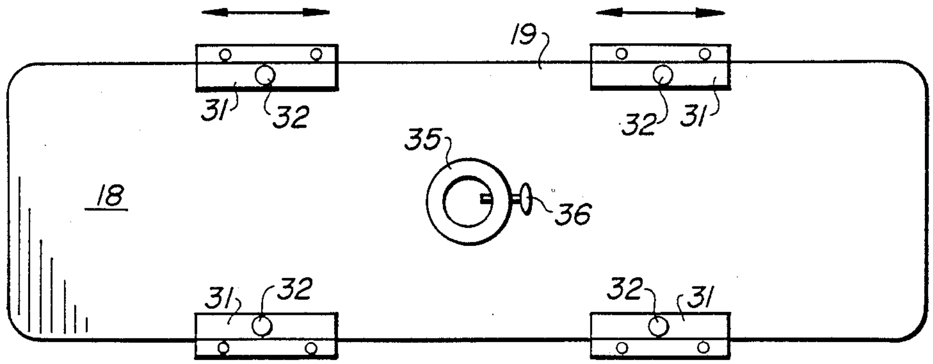
FIG. 6 is a bottom plan view of the shoulder support system of FIGS. 4 and 5, shown in a position intermediate to FIGS. 4 and 5.
Figure 8:
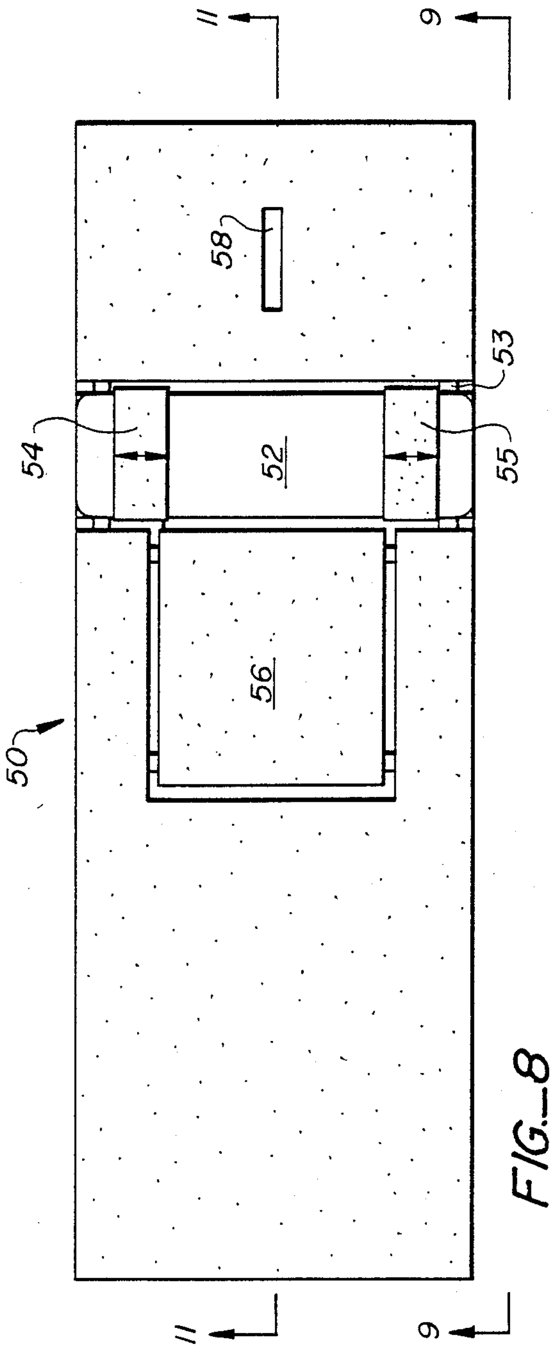
FIG. 8 is a top plan view of the table of FIG. 7.
Figure 9:
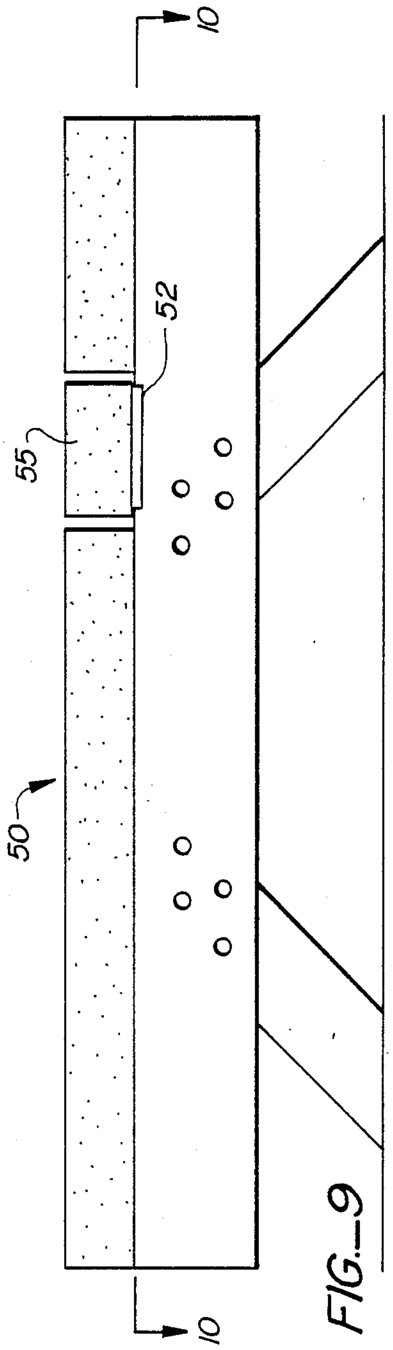
FIG. 9 is a view in side elevation of the table of FIGS. 7and 8, looking in the direction of the arrows 9—9 in FIG. 8.
Figure 10:
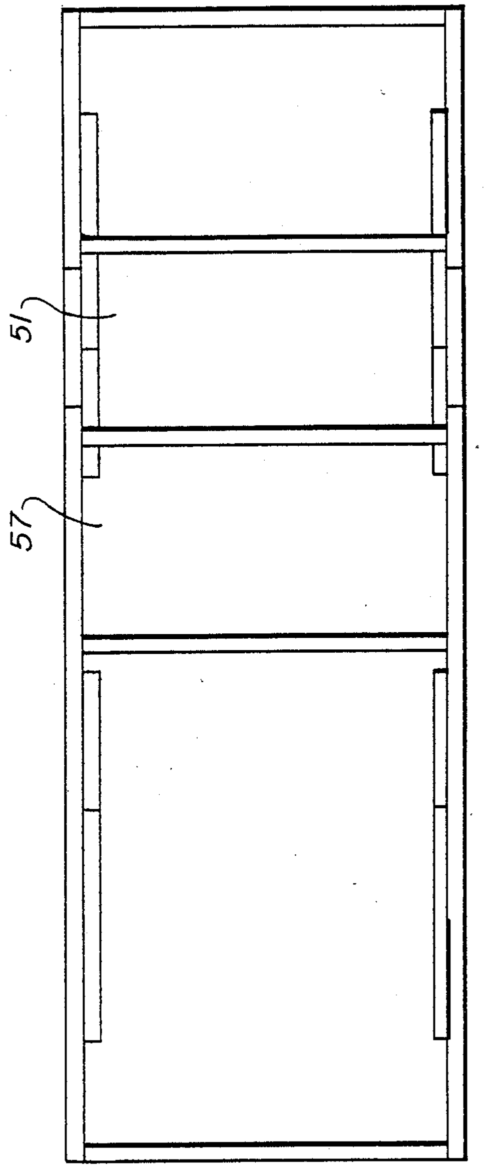
FIG. 10 is a bottom view of the table of FIGS. 7-9.
Figure 11:
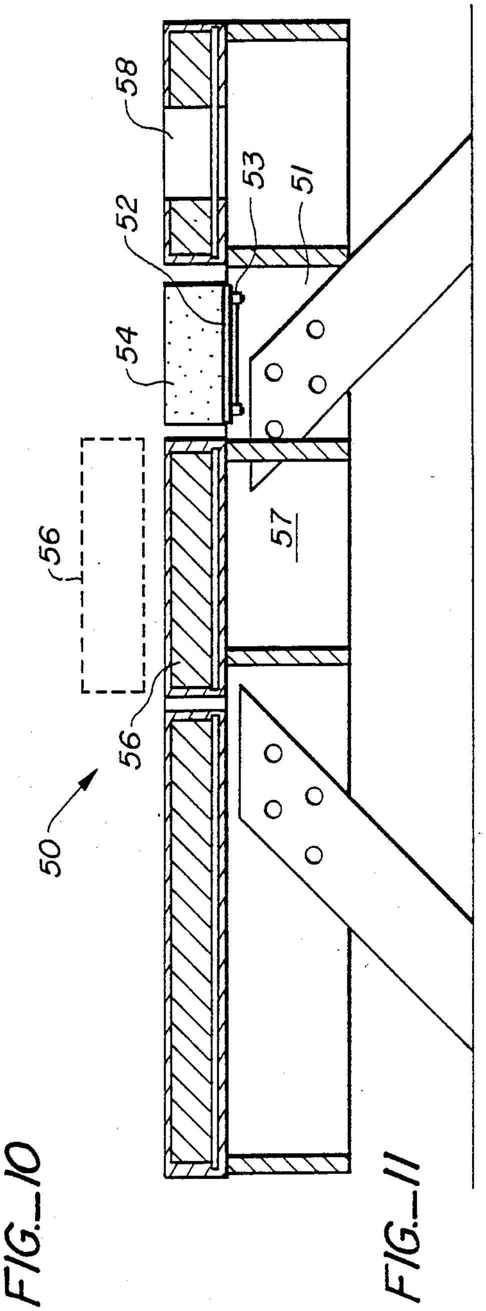
FIG. 11 is a view in section taken along the line 11—11 in FIG. 8.

FIGS. 4, 5, and 6 illustrate different lateral positions in which the shoulder support members 22 and 23 may be adjusted. The two shoulder support members 22 and 23 may be moved along the base bracket tracks 19 laterally with respect to the table 10 to accommodate patients having different shoulder widths. The shoulder supports 22 and 23 may be moved substantially against each other when no patient is to lie face down on the table.

FIGS. 7-11 show a simplified table 50, lacking many of the adjustments provided by the supports 12, 13, and 14, but including a well 51 in which is located a base 52, like the base 18, with tracks 53 along which shoulder support members 54 and 55 may slide and, when set in the proper position, provide the needed shoulder support and breast stress relief. The well 51 may be open at each end as shown. The upper surface of the table 50 is substantially flat and coplanar.

A removable panel 56 may lie over a second well 57 where further relief may be provided for a pregnant woman. Padding may be provided for the surfaces where desired. For chiropractic treatment, the table 50 may be 27 inches wide, and the well 57 may be about 19 inches wide, 10 inches long and about 5 inches deep. The table surface may be about 21 inches high, or, for massages, the height may be about 40 inches above the floor level. A nose-receiving well 58 may also be provided, as in some devices already known.

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. A chiropractic treatment table, comprising:

a table substructure, patient support means for supporting a recumbent patient, said support means being mounted on said substructure and having a normally flat patient support surface for support of most of the body of the patient with a first well leading down therethrough and a pair of guide means extending laterally thereacross so that said first well lies between said guide means, means for reducing stress on the chest or breast area of a patient comprising a pair of separated shoulder support means, each having support surfaces and being movably supported by said guide means for supporting a patient's upper body by the shoulders when the patient is lying on the table, means mounting said shoulder support means on said guide mass for movement laterally apart from each other along said guide means to provide in said first well between them a recess the size of which is varied by moving said shoulder support means, whereby a patient can lie face down on said patient support means and be supported by the body with the shoulders resting on the support surfaces of the shoulder support means and, where the patient is a woman, her breasts will rest in said recess between said support surfaces, to provide breast stress relief.

2. The treatment table of claim 1, including a second well spaced from the first said well and spaced therefrom in the area of the patient's body below the breasts, and a removable panel generally coplanar with said shoulder support means, normally covering said second well and opening said second well when said panel is removed, to provide special stress relief for pregnant women.

3. An improved chiropractic treatment table of the type which has a table substructure on which are mounted a plurality of table members which can be independently adjusted with the table substructure to various positions for supporting a patient chiropractic treatment, the improvement comprising: a base mounted to said table substructure, means for reducing stress on the chest or breast area of a patient comprising a pair of separated shoulder support means for supporting the shoulders of a patient lying on said table members, each having support surfaces and being supported by said base for supporting a patient's shoulder's when the patient is lying on the table means mounting said shoulder support means for movement on said base, said shoulder support means being laterally apart from each other to provide a recess between the support surfaces of the two shoulder support means, whereby a patient can lie face down on the improved table and be supported by the shoulders resting on the support surfaces of the shoulder support means and, where the patient is a woman, her breasts will rest in the recess between said support surfaces, so that the table does not exert substantial force on the patient's breasts.

4. The treatment table of claim 3, including adjustment means for adjusting the position of said shoulder support means, both laterally and vertically, independently, with respect to the table so that the shoulders of patients having different shoulder widths can be properly supported.

5. The treatment table of claim 4, wherein said adjustment means includes two brackets on which the shoulder support means are mounted and a bracket track on said base on which said brackets are slidably mounted for movement laterally with respect to the table.

6. The treatment table for claim 5, wherein the brackets each include locking means for fixing the brackets and shoulder support means at a particular position relative to the bracket track to prevent the shoulder support means from moving during treatment.

7. The treatment table of claim 5, having elevator means secured between and in contact with said base and said substructure, for moving said brackets and said shoulder support means up and down to increase or decrease the height of said shoulder support means.

8. The treatment table of claim 5, wherein the bracket track comprises a rectangular piece of rigid material secured to said base.

9. The shoulder support means of claim 1, including adjustment means for adjusting the position of the shoulder support means laterally with respect to each other and to the table so that the shoulders of patients having different shoulder widths can be properly supported and have the correct length and width of recess.

10. The shoulder support system of claim 9, wherein the adjustment means includes a support bracket for each shoulder support means, an auxiliary base supported by said substructure, a bracket track on said base, said brackets being slidably mounted on said track for movement laterally with respect to the table.

11. The shoulder support system of claim 10, wherein each said support bracket includes locking means for fixing the position on the bracket of the shoulder support means at a particular point on the bracket track, to prevent the shoulder support means from moving during treatment.

12. The shoulder support system of claim 10 having elevating means positioned between and engaging said base and said substructure for raising and lowering said support means relative to said substructure.

13. The system of claim 10, wherein the bracket track comprises a rectangular piece of rigid material secured to said base.

* * * * *

UNITED STATES PATENT AND TRADEMARK OFFICE
CERTIFICATE OF CORRECTION

PATENT NO. : 4,903,689

DATED : February 27, 1990

INVENTOR(S) : Lannertone, Marc W.

It is certified that error appears in the above-identified patent and that said Letters Patent are hereby corrected as shown below:

ON TITLE PAGE:

In the References Cited, U.S. PATENT DOCUMENTS "3,795,018 3/1974 B//aded........" should read --3,795,018 3/1974 Broaded--.

Column 5, line 19,
"guide mass for" should read -guide means for--

Column 5, line 42,
"a patient chiropractic" should read --a patient for chiropractic--.

Signed and Sealed this

Twenty-fifth Day of February, 1992

Attest:

HARRY F. MANBECK, JR.

*Attesting Officer* *Commissioner of Patents and Trademarks*